(12) United States Patent
Kamiyama et al.

(10) Patent No.: US 8,284,395 B2
(45) Date of Patent: Oct. 9, 2012

(54) WAFER SURFACE MEASURING APPARATUS (75) Inventors: Eiji Kamiyama, Tokyo (JP); Etsurou Morita, Tokyo (JP)

(73) Assignee: Sumco Corporation, Tokyo (JP)

( * ) Notice: Subject to any disclaimer, the term of this patent is extended or adjusted under 35 U.S.C. 154(b) by 442 days.

(21) Appl. No.: 12/699,955

(22) Filed: Feb. 4, 2010

(65) Prior Publication Data

US 2010/0201976 A1 Aug. 12, 2010

(30) Foreign Application Priority Data

Feb. 12, 2009 (JP) ................................. 2009-029952

(51) Int. Cl.
*G03B 27/52* (2006.01)
(52) U.S. Cl. .................................................... 356/237.5
(58) Field of Classification Search .................. None
See application file for complete search history.

(56) References Cited

U.S. PATENT DOCUMENTS 6,179,921 B1 * 1/2001 Ruffell et al. ................. 118/715
6,875,987 B2 * 4/2005 Kondo ..................... 250/442.11
2009/0305021 A1 12/2009 Ohkubo

FOREIGN PATENT DOCUMENTS

| JP | 10-156781 | 6/1998 |
| JP | 2003-303878 | 10/2003 |
| JP | 2008-267827 | 11/2008 |

* cited by examiner

*Primary Examiner* — Tu Nguyen
(74) *Attorney, Agent, or Firm* — Greenblum & Bernstein, P.L.C.

(57) ABSTRACT

A wafer surface measuring apparatus which measures a surface of the wafer by irradiating a laser beam on a wafer comprising a measuring stage that supports the outer edge of the wafer and loads the wafer in a manner not contacting the rear surface of the wafer and the stage surface, a wafer carrying means that moves the wafer over the measuring stage and loads the wafer on the measuring stage from an upward side, a rotary drive unit which rotates the measuring stage, and an ejection hole formed at a center portion of the stage surface to supply gas to a rear surface of the wafer loaded on the measuring stage. The wafer carrying means includes a chuck which sucks and holds the surface of the wafer in a non-contact manner and bends the wafer in an upwardly convex shape.

10 Claims, 10 Drawing Sheets

WAFER SURFACE MEASURING APPARATUS

BACKGROUND OF THE INVENTION

1. Field of the Invention

The present invention relates to a wafer surface measuring apparatus capable of detecting foreign substances, such as particles or the like, or fine defects existing on the surface of a semiconductor wafer by using light scattering.

Priority is claimed on Japanese Patent Application No. 2009-029952, filed Feb. 12, 2009, the content of which is incorporated herein by reference.

2. Description of the Related Art

Up to now, a wafer surface measuring apparatus of a laser scattering type has been known as an apparatus for detecting foreign substances, such as particles or the like, or fine defects existing on the surface of a semiconductor wafer (hereinafter, referred to as a wafer). The wafer surface measuring apparatus can perform detection of particles or defects by irradiating a laser beam on the wafer which is loaded on a measuring stage and rotated at high speed and detecting scattered light from the wafer surface. Prior art is disclosed in, for example, Japanese Unexamined Patent Application Publication No. 2008-267827.

In such a wafer surface measuring apparatus, if carrying of the wafer to the measuring stage is manually performed, working efficiency is low, and the possibility of contamination of the wafer, such as by particle adhesion, is high, because of the interposition of manual working. Consequently, such a wafer surface measuring apparatus is generally located in a box-shaped clean room. The wafer surface measuring apparatus is configured to discharge the wafer from a cassette, which is carried to the clean room, by using an arm, and then carry the wafer to the measuring stage.

Meanwhile, when the wafer is carried by the arm, only the outer edge of the wafer is supported by the arm in order to prevent flaws from being produced on the rear surface thereof, or particles from adhering to the rear surface, since the finishing of the front and rear surfaces of the wafer is to a mirror surface. In the state in which the wafer is loaded on the measuring stage, only the outer edge thereof is supported, so that the rear surface of the wafer does not come in contact with the stage surface.

In the case in which the wafer is loaded on the measuring stage, the center portion of the wafer is bent downward by its own weight. Therefore, when the wafer is measured, the wafer surface measuring apparatus of the related art ejects gas for upper wafer from a center portion of the stage surface which loads the wafer, so that the bending of the wafer is corrected by pressure of the gas (For example, see Japanese Unexamined Patent Application Publication No. 2003-303878). As a result, the non-contact state between the rear surface of the wafer and the stage surface of the measuring stage is maintained and flatness of the surface of the wafer is maintained, thereby performing the measurement with high accuracy.

The above-described wafer surface measuring apparatus can deal with a wafer having a diameter of 300 mm or less at present, but it will be necessary to deal with a wafer having a diameter of 450 mm in the future. However, in the case of a large-diameter wafer, since bending of the center portion of the wafer due to its own weight is increased when the wafer is loaded on the measuring stage, a problem may happen in that the center portion of the wafer comes into contact with the stage surface before the outer edge of the wafer is supported. Even though the diameter of the wafer is 300 mm like the past, if the thickness of the wafer is thin, the bending amount increases. Thus, the wafer comes in contact with the stage.

It is conceivable that contact between the wafer and the stage can be avoided by increasing the space between the rear surface of the wafer and the stage surface. In this instance, there is a problem in that since turbulent flow is produced when the gas ejected from the center portion of the stage passes through the gap between the rear surface of the wafer and the stage surface, the wafer is vibrated or particles are generated.

The invention has been made to take the above problem into consideration, and an object of the invention is to provide a wafer surface measuring apparatus capable of supporting a wafer having a large diameter or thin thickness on a measuring stage in a state of non-contact between a rear surface of the wafer and the measuring stage.

SUMMARY OF THE INVENTION

The invention proposes the following means taking the above problem into consideration.

That is, a wafer surface measuring apparatus according to the invention which measures a surface of the wafer by irradiating a laser beam on the wafer, including a measuring stage that supports the outer edge of a wafer and loads the wafer in a manner not contacting the rear surface of the wafer and the stage surface; a wafer carrying means that moves the wafer over the measuring stage and loads the wafer on the measuring stage from the upward side; a rotary drive unit which rotate the measuring stage; and an ejection hole formed at a center portion of the stage surface to supply gas to a rear surface of the wafer which is loaded on the measuring stage, wherein the wafer carrying means includes a chuck that sucks and holds the surface of the wafer in a non-contact manner and bends the wafer in an upwardly convex shape, the chuck supporting the wafer in the upwardly convex shape when the wafer is held.

Here, the term 'rear surface of the wafer' means the surface opposite to the surface of a flat portion serving as a main surface of the wafer on which a device fabricating region is faulted, and the term 'outer edge' means a portion having a chamfered portion positioned at the periphery of the main surface of the wafer and the surface of the thickness direction. The term 'supports the wafer in a state it is bent in an upwardly convex shape' means the support of the wafer in the state in which the center portion of the wafer is positioned at a higher position relative to the edge portion of the wafer or the center portion of the wafer protrudes towards the chuck side higher than the edge portion of the wafer. In particular, it means the support of the wafer in the state in which the center portion of the surface of the wafer, of which the main surface is positioned in a horizontal direction, is sucked by the chuck from the upper side, so that the edge portion of the wafer is bent downward by its own weight.

The chuck may be located at a position which can support the wafer in a state in which it is bent in the upwardly convex shape, with the wafer being maintained in a non-contact state. For example, the chuck may be set up in a region of the center portion of the wafer which is in a range of two-thirds of the radius of the wafer, more preferably, in a region of the center portion of the wafer which is in a range of half of the radius of the wafer, or may be set up in a region of the center portion of the wafer which is in a range of one-third of the radius of the wafer.

According to the wafer surface measuring apparatus of the present invention, since the wafer is bent in the upwardly convex shape in the state in which the surface thereof is held in a non-contact manner by the wafer carrying means, the wafer can be approached and loaded on the measuring stage, with the distance between the center portion of the wafer and the measuring stage being maintained largely compared with the distance between the edge portion of the wafer and the measuring stage. Therefore, it is possible to prevent the center portion of the wafer from coming in contact with the stage surface ahead of the edge portion of the wafer, when the wafer is loaded on the measuring stage. In this instance, the surface of the wafer is held in the non-contact state by the Bernoulli chuck. Consequently, the carrying, loading and measuring of the wafer can be performed by maintaining the non-contact state of the front surface and the rear surface of the wafer.

According to the wafer surface measuring apparatus of the present invention, when the wafer is loaded on the measuring stage by the wafer carrying means, the gas may be supplied from the ejection hole.

When the wafer is loaded on the measuring stage, the center portion of the wafer is lower than the edge portion of the wafer due to the wafer's own weight, compared with the state in which the center portion is held by the chuck, at the time the holding by the chuck is released. In this instance, since the center portion of the rear surface of the wafer is pressed upward by the pressure of the gas supplied from the ejection hole, it is possible to diminish the height position of the center portion of the wafer from being lowered. Therefore, it is possible to surely prevent the rear surface of the wafer and the stage surface from coming in contact with each other. In addition, it is possible to bend the wafer in the further upwardly convex portion by properly controlling the quantity of the gas ejected from the ejection hole based on the diameter, weight and thickness dimension of the wafer, thereby preventing the rear surface of the wafer and the stage surface from coming in contact with each other.

In the state in which the suction and holding of the wafer by the chuck is released and then the wafer is loaded on the measuring stage, the center portion of the rear surface of the wafer is pressed upward by pressure of the gas supplied from the ejection hole. Therefore, it is possible to prevent the rear surface of the wafer from coming in contact with the stage due to the bending caused by its own weight.

Further, according to the wafer surface measuring apparatus of the present invention, when the wafer is loaded on the measuring stage, pressure of the gas supplied from the ejection hole is set to be higher than pressure of the gas supplied from ejection hole at measuring time of the wafer. The ejection amount of the gas is set in such a way that at the measuring time of the wafer, the bending is disappeared, and the surface of the wafer becomes flat.

When the suction and holding of the wafer by the chuck is released, the wafer is still bent in the upwardly convex portion by the chuck, but due to the restoring force and its own weight, the center portion of the wafer is deflected downward, and thus is likely to come in contact with the stage surface. Since it starts to eject the gas from the ejection hole before the suction and holding by the chuck is released and simultaneously the pressure of the gas supplied from the ejection hole is increased at the releasing time of suction and holding, the pressure can be strongly applied to the center portion of the wafer upwardly at the rear surface thereof. As a result, it is possible to surely prevent the rear surface of the wafer from coming in contact with the stage surface. The release of the suction and holding by the chuck is performed after the edge portion of the wafer comes in contact with the measuring stage, the gas ejection from the ejection hole is started before the edge portion of the wafer comes in contact with the measuring stage, and the gas ejection state can be maintained.

After the measurement of the wafer surface is completed, it is preferable that the gas is ejected until re-holding of the wafer by the chuck is started and the edge portion of the wafer is spaced apart from the measuring stage. In addition, before re-holding by the chuck is restarted after the measurement completion, it is preferable that an ejection quantity of the gas is set to be equal to that when the suction and holding is released.

According to the wafer surface measuring apparatus of the present invention, the wafer carrying means may include a rotational position adjusting means for displacing a rotational position of the wafer, and a notch sensor for detecting a position of a notch of the wafer. Here, the term 'displace the rotational position of the wafer' means that the wafer held by the wafer carrying means can be rotated around the central axis of the main surface of the wafer as the rotation axis.

Therefore, immediately before the wafer is loaded at the time of carrying the wafer by the wafer carrying means, the position of the notch of the wafer is aligned, and then the wafer can be loaded on the measuring stage in this state, so that it is not necessary to perform separate position aligning work of the notch, thereby promoting work efficiency.

The chuck can be selected from an electrostatic chuck or a Bernoulli chuck.

In addition, according to the wafer surface measuring apparatus of the present invention, the pressurized gas supplied to the Bernoulli chuck may be clean gas having improved cleanliness which passes through an air filter. As a result, the cleanliness on the surface of the wafer can be highly maintained.

The clean gas passing through the air filter has a cleanliness of a range which does not exert an effect on the measurement by the measuring apparatus, and, for example, the cleanliness is set to be approximately equal to that of ambient gas in the measuring stage. The gas supplied from the same supply source as the gas ejected from vicinity of the center portion of the measuring stage may be used as the pressurized gas of the Bernoulli chuck.

According to the wafer surface measuring apparatus of the present invention, the wafer carrying means may include a cover having a diameter larger than the wafer so as to cover the whole area of the wafer when seen from a plan view, and being installed in parallel with the wafer in a facing state when the main surface of the wafer is horizontally held at an upper side. Therefore, it is possible to prevent particles and foreign materials which are dropped over the wafer during wafer carrying from adhering to the surface of the wafer, thereby highly maintaining the cleanliness of the surface of the wafer before and after the measurement of the wafer's surface.

In addition, according to the wafer surface measuring apparatus of the present invention, the wafer carrying means may include a gas supplying means for supplying gas to prevent ambient air from entering between the cover and the surface of the wafer.

In this way, it is possible to further surely prevent foreign materials from adhering to the surface of the wafer, thereby highly maintaining the cleanliness of the surface of the wafer. In this instance, a gas ejection hole for ejecting gas to the vicinity of the center portion of the wafer at a space between the held wafer and the cover may be provided at a surface of the cover facing the wafer. In this instance, the ejection quantity of the gas may be set in such a way that a gas flow is produced in the space between the wafer and the cover to a certain degree which can prevent particles or foreign substances from adhering to the surface of the wafer or prevent foreign substances or air containing foreign substances from entering the space from the exterior.

According to the wafer surface measuring apparatus of the present invention, it may further include a wafer discharging means for discharging the wafer from a cassette with the plurality of wafers received therein, in which the wafer carrying means sucks, holds and carries the wafer discharged from the cassette by the wafer discharging means.

According to the wafer surface measuring apparatus having such features, in the case in which the wafer carrying means including the chuck such as the Bernoulli chuck or the like has a size so as not to enter between plural wafers received in parallel in the cassette, it is possible to easily carry the wafer from the cassette to the measuring stage. This can be performed by discharging the wafer from the cassette with a separate wafer discharging means and then holding the wafer by the wafer carrying means to the measuring stage.

With the wafer surface measuring apparatus of the present invention, since the wafer is sucked and held by the chuck of the wafer carrying means in the state the wafer is bent in an upwardly convex shape, it can load the wafer having a large diameter or thin thickness on the measuring stage in a non-contact state of the rear surface of the wafer and the measuring stage.

DETAILED DESCRIPTION OF THE INVENTION

Figure 1:
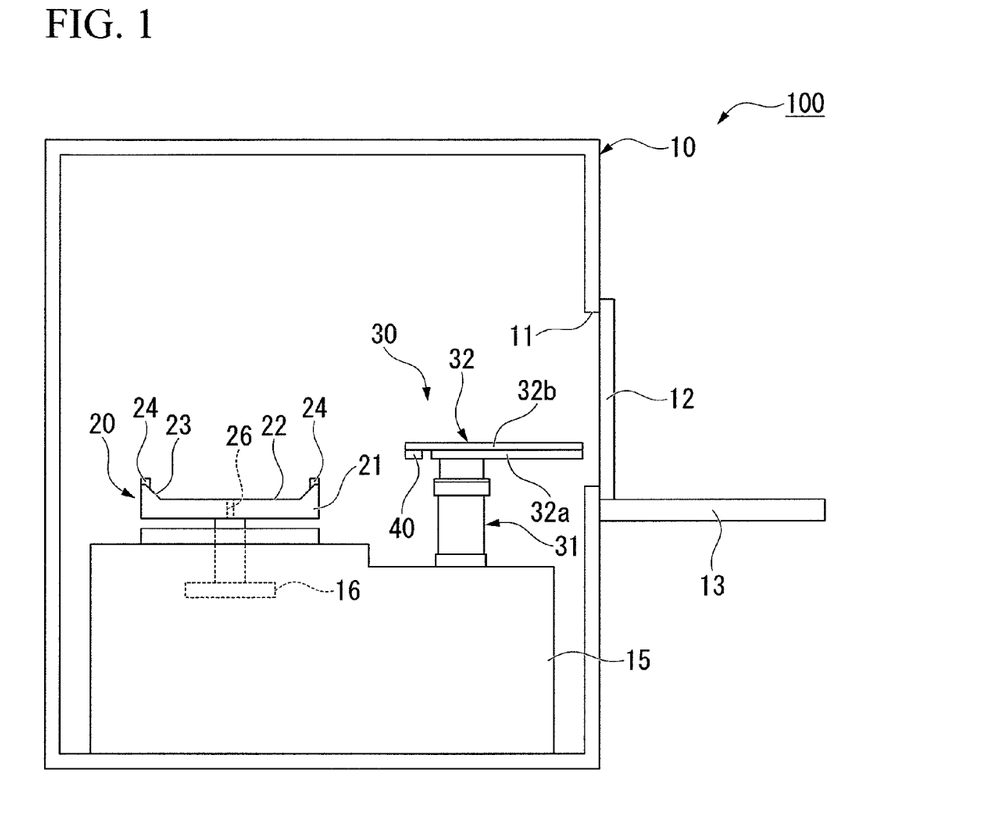
FIG. 1 is a configuration diagram schematically illustrating one example of a wafer surface measuring apparatus according to the invention.

Now, an embodiment of the invention will be described with reference to the accompanying drawings. FIG. 1 is a configuration diagram schematically illustrating one example of a wafer surface measuring apparatus according to the invention. A wafer surface measuring apparatus 100 can detect foreign substances, such as particles, fine defects, flaws or the like existing on a surface of a semiconductor wafer W by a laser beam. In this embodiment, measurement of a large-diameter wafer W having a diameter of 300 mm or 450 mm is performed prior to a process of fabricating LSIs.

The wafer surface measuring apparatus 100 includes a clean room 10, a measuring stage 20 and a wafer carrying device (a wafer carrying means) 30 which are provided in the clean room 10. The wafer surface measuring apparatus 100 is provided with a measuring unit constituted by a laser light source, an optical detector or the like, but the measuring unit is not shown in FIG. 1.

The clean room 10 is formed in a rectangular box shape, and a base 15 is installed in the clean room. A rotary drive unit 16 which rotate the measuring stage with a wafer W loaded on is constituted inside the base 15. At a sidewall of the clean room 10, a wafer receiving port 11 is opened to communicate inside and outside of the clean room 10, and the wafer receiving port 11 can be opened or closed by a shutter 12. The shutter 12 is generally closed, and thus the wafer receiving port 11 is in a closed state, so that the inside of the clean room 10 is in a sealed state and is maintained in high cleanliness. In order to increase the cleanliness in the inside of the clean room 10, a clean unit (not shown) for maintaining a clean atmosphere in the clean room 10 by using clean air may be installed.

Just below the wafer receiving port 11 outside the clean room 10, a cassette mounting stage 13 is fixed to an outer wall of the clean room 10. On the cassette mounting stage 13, a cassette 90, in which plural sheets of stacked wafers W to be measured are received, is mounted (for example, see FIG. 5).

Figure 2:
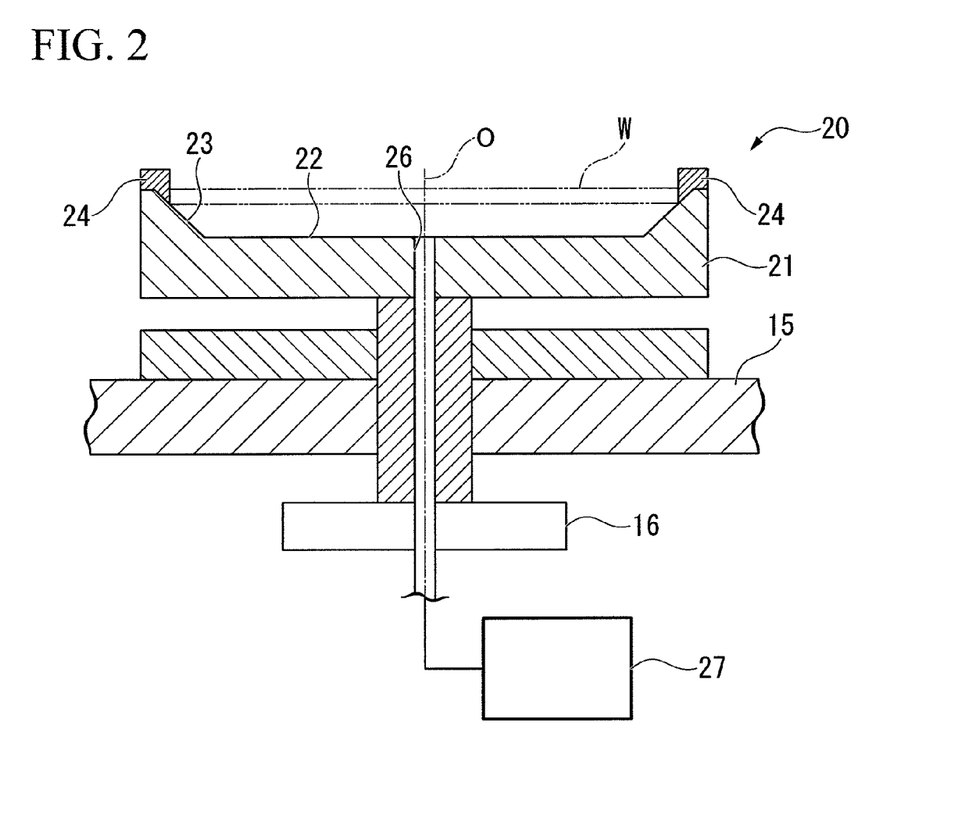
FIG. 2 is a cross-sectional view of a measuring stage.

The measuring stage 20 loads the wafer W to be measured, and is installed on the base 15 in the clean room 10. More specifically, as shown in FIG. 2, the measuring stage 20 is formed in the shape of a substantially circular disc, and has a stage body 21 rotating by a rotary drive unit 16 around an axis O which extends in a vertical direction.

A circular stage surface 22 of a flat shape is formed on the upper surface of a stage body 21, and a tapered support surface 23 which is inclined upward towards the radial outer side of the stage body 21 is formed on an outer circumference portion of the stage surface 22.

The area of the stage surface 22 is smaller than the surface and the rear surface of the wafer W. Consequently, if the wafer W is loaded on the stage body 21 from an upper side, the whole region of the outer edge (that is, an edge of the wafer W which forms a circular disc) of the wafer W comes in contact with the tapered support surface 23.

In this way, the wafer W is loaded on the stage body 21 in such a way that the rear surface of the wafer W does not come in contact with the stage surface 22.

The outer edge of the upper surface of the stage body 21 is provided with a plurality of protrusions 24 for positioning the wafer W protruding from the outer circumference thereof at regular intervals. The horizontal movement of the wafer W on the stage body 21 is restricted by the protrusions 24.

In addition, the stage surface 22 is provided at a center portion thereof with an ejection hole 26 which is extended in the axis O. The ejection hole 26 is formed to upwardly supply gas supplied from the gas supply device 27. Pressure of the gas can be properly adjusted by the gas supply device 27.

The wafer carrying device 30 is adapted to carry and load the wafer W on the measuring stage 20. As shown in FIG. 1, the wafer carrying device 30 is installed near by the wafer receiving port 11 rather than the measuring stage 20 on the base 15, and includes a movable support post 31, an arm 32 and a Bernoulli chuck 40.

The movable support post 31 is vertically arranged on the base 15, and is controlled to be telescopically moved in upward and downward directions.

The arm 32 is constituted by a first arm 32a having a proximal end which is rotatably connected to an upper leading end of the movable support post 31 and extended in a horizontal direction, and a second arm 32b rotatably connected to the leading end of the first arm 32a and extended in the horizontal direction in the same way. Amounts of pivotal movement of the first arm 32a and the second arm 32b are respectively controlled, so that the arm 32 can be freely pivoted over the movable support post 31.

Figure 3:
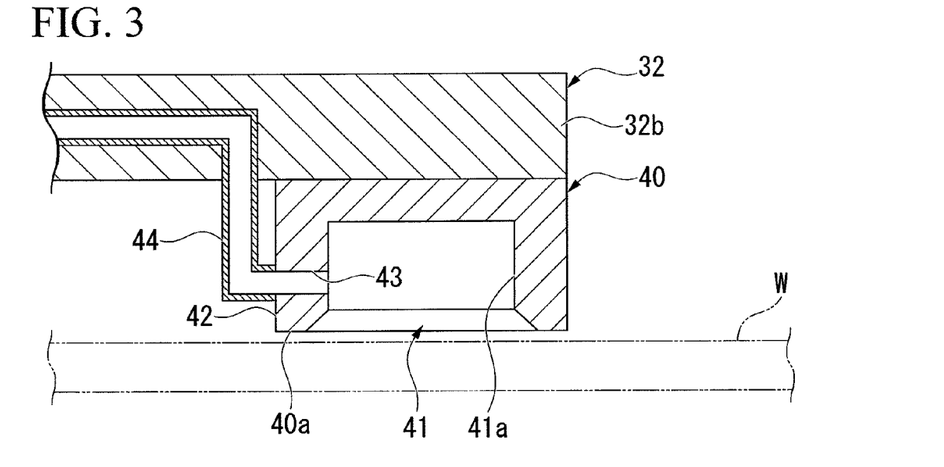
FIG. 3 is a cross-sectional view of a Bernoulli chuck in a wafer carrying means.

The Bernoulli chuck 40 is adapted to suck the surface of the wafer W. More specifically, as shown in FIG. 3, the Bernoulli chuck 40 is fixed to a downwardly facing surface of the leading end of the second arm 32b.

The Bernoulli chuck 40 is formed in the shape of cylinder having a bottom, and is provided with a concave portion 41 which is downwardly opened, at the center portion of the downwardly facing chuck surface 40a. The Bernoulli chuck is provided with a fluid introduction channel 43 which communicates with an inner peripheral wall surface 41a and an outer peripheral cylindrical surface 42, and a fluid piping 44 is connected to the outer peripheral cylindrical surface 42 of the fluid introduction channel 43. Further, the fluid piping 44 is connected to a pressurized gas supply source (not shown). In this way, the pressurized gas supplied from the pressurized gas supply source is fed to the concave portion 41 through the fluid piping 44 and the fluid introduction channel 43.

As such, if the pressurized gas is fed to the concave portion 41 of the Bernoulli chuck 40, a swirling flow is produced along the inner peripheral wall surface 41a of the concave portion 41. In this instance, if the wafer W exists at a position facing the chuck surface 40a, the supply of atmospheric pressure to the concave portion 41 from the exterior is restricted. Accordingly, since density of air per unit area is gradually decreased due to the centrifugal force of the swirling flow, the pressure at the center portion of the swirling flow is decreased to generate a negative pressure. The wafer W is pressurized by peripheral atmospheric pressure and is thus sucked to the chuck surface 40a by the negative pressure. If the chuck surface 40a comes close to the wafer W, the discharge of the air from the concave portion 41 is restricted. As a result, because the velocity of the air fed to the concave portion 41 from the fluid introduction channel 43 becomes slow, the pressure at the center portion of the swirling flow in the concave portion 41 is increased, so that the wafer W does not come in contact with the chuck surface 40a and the distance between the chuck surface 40a and the wafer W is maintained. The wafer W is consistently maintained by the air interposed between the chuck surface 40a and the wafer W.

Preferably, the pressurized gas supplied to the Bernoulli chuck 40 has clean gas having cleanliness which passes through an air filter. In this way, it is possible to prevent foreign substances from adhering to the surface of the wafer W, thereby maintaining the cleanliness on the surface of the wafer W.

Next, the process of measuring the wafer W by the wafer surface measuring apparatus 100 having the above-described configuration will be described with reference to a flowchart of FIG. 4 and FIGS. 5 to 8.

Figure 4:
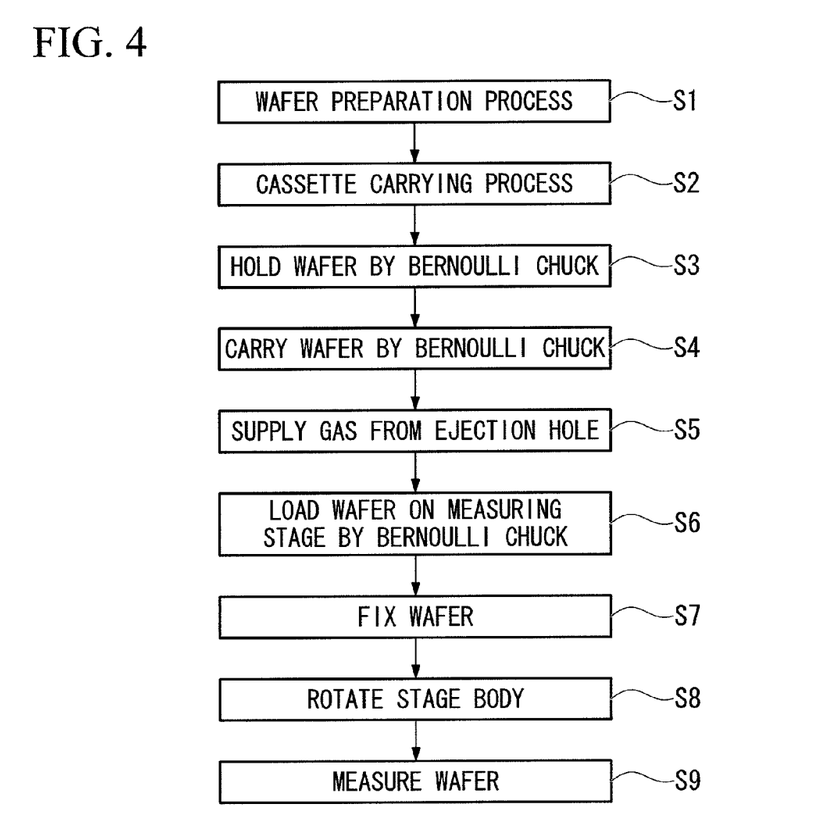
FIG. 4 is a flowchart illustrating a process of measuring a wafer in a wafer surface measuring apparatus.

A wafer preparation process (step S1) shown in FIG. 4 is a process in which the silicon single crystal is pulled up from a silicon melt by a CZ (Czochralski) method, the silicon single crystal is subjected to slice machining and surface treatment such as chamfering, grinding, polishing, washing or the like, and then a wafer is prepared by a polishing process. Such a wafer W is received in each of plural shelves of the cassette 90, as shown in FIG. 5, the shelves being placed at an interval in a vertical direction.

In a cassette carrying process S2, the cassette 90 is carried to and loaded on the cassette mounting stage 13 of the wafer surface measuring apparatus 100. After that, the shutter 12 of the wafer surface measuring apparatus 100 is opened, so that the inside of the clean room 10 is communicated with the inside of the cassette 90 through the wafer receiving port 11.

Figure 5:
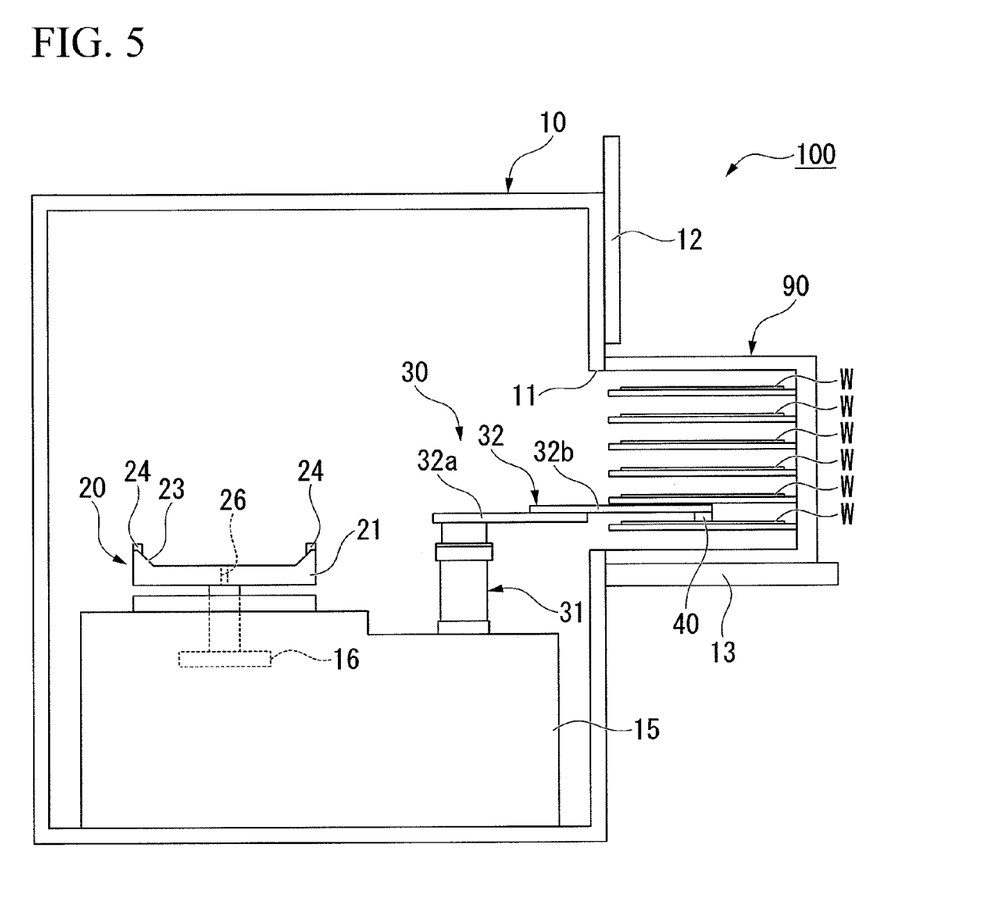
FIG. 5 is a diagram illustrating a state in which a wafer carrying means carries a wafer out from a cassette transported in a wafer surface measuring apparatus.

And then, as shown in FIG. 5, the arm 32 of the wafer carrying device 30 in the clean room 10 enters into the cassette 90 through the wafer receiving port 11, and the center portion of the surface of the wafer W is sucked and held by the Bernoulli chuck 40 in a non-contact relation (step S3). The wafer carrying device 30 can suck the wafer W of a certain shelf by expansion and contraction of the movable support post 31. The arm 32, to which the Bernoulli chuck 40 is fixed, has a size so that it enters into the cassette 90.

Figure 6:
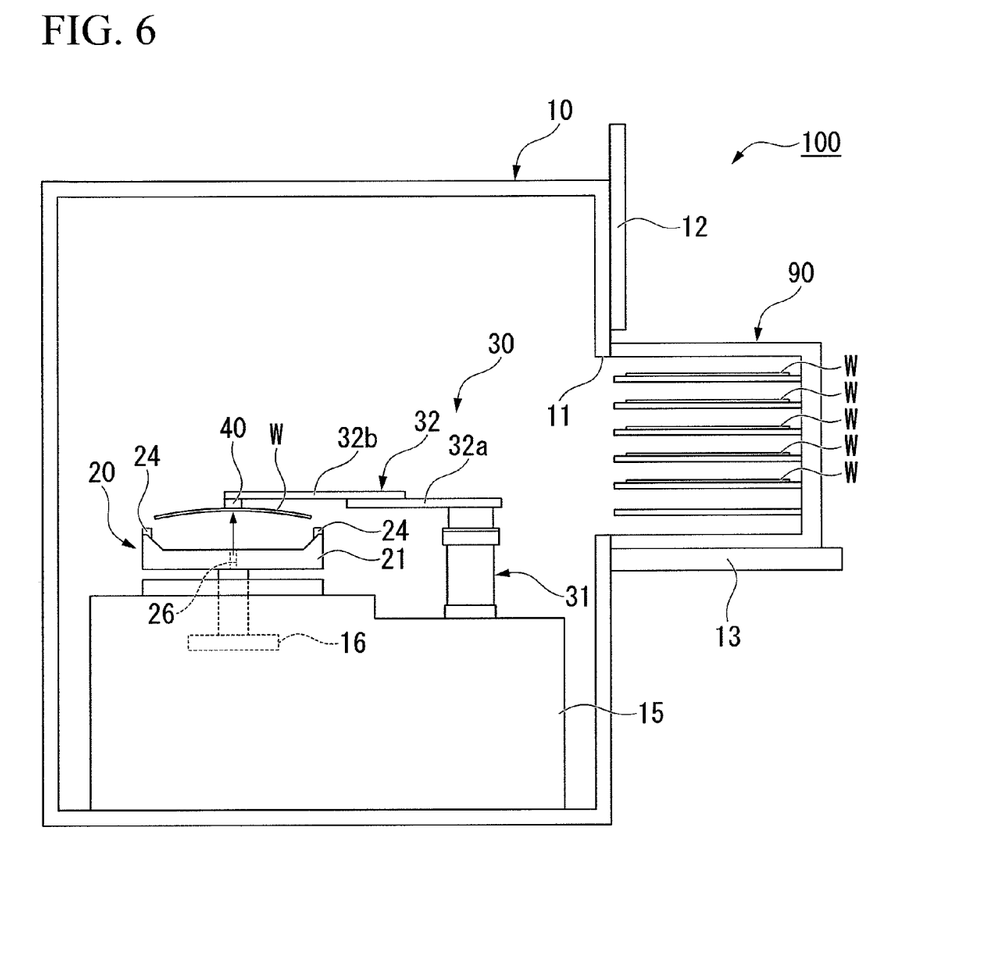
FIG. 6 is a diagram illustrating a state in which a wafer is moved upward from a measuring stage by a wafer carrying means.

As the arm 32 pivots and moves and simultaneously the movable support post 31 expands and contracts, the wafer W is carried to the upper portion of the measuring stage 20 (step S4). In this instance, since the center portion of the surface of the wafer W is sucked and held by the Bernoulli chuck 40, an edge of the wafer which is apart from the center portion in a radial direction is bent downward by its own weight, as shown in FIG. 6. That is, in this embodiment, since the center portion of the wafer W is sucked and held by the Bernoulli chuck 40, the wafer W can be bent in an upwardly convex shape.

In such a way, when the wafer W is moved over the measuring stage 20, the gas is supplied upward from the ejection hole 26 formed at the center portion of the stage surface 22 (step S5). At the measuring time of the wafer W, the gas is ejected from the ejection hole 26, but the gas supply device controls the pressure of the supplied gas in such a way that the pressure of the gas at step S5 is higher than the pressure of the gas at the measuring time of the wafer W.

Figure 7:
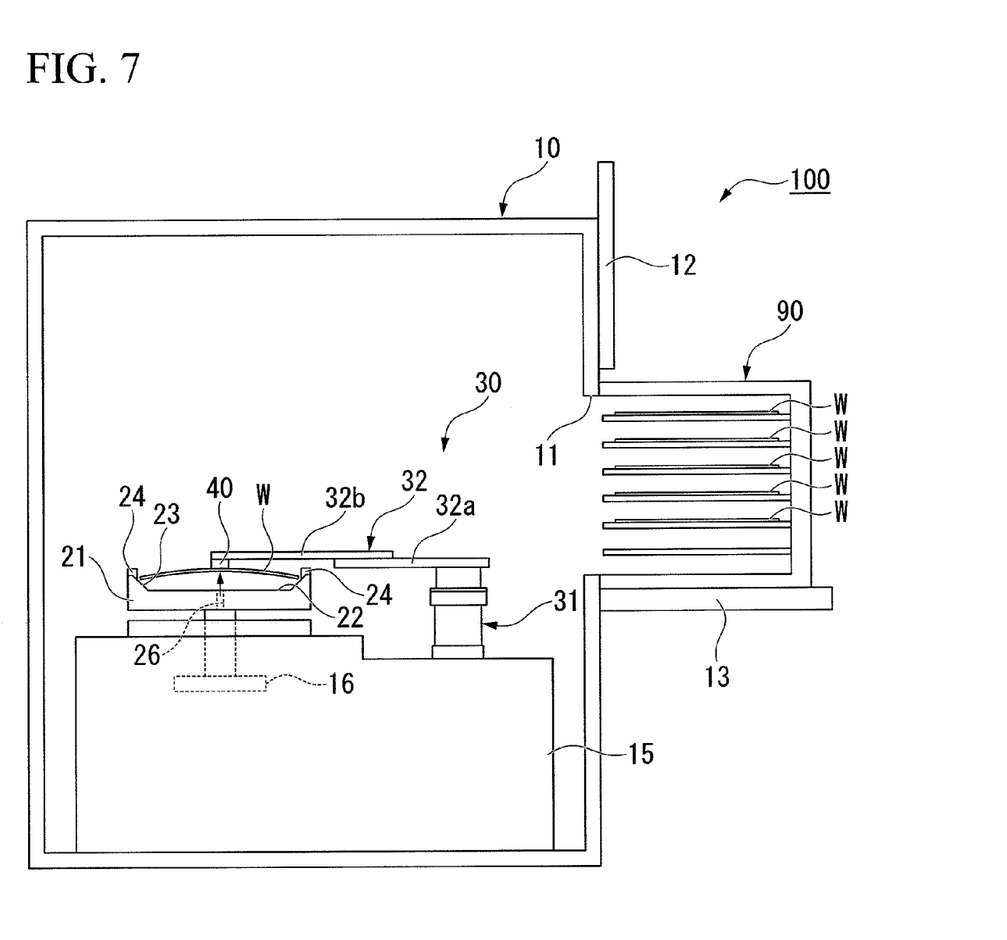
FIG. 7 is a diagram illustrating a state in which a wafer is being loaded on a measuring stage.

As shown in FIG. 7, the movable support post 31 of the wafer carrying device 30 is lowered in the state in which the gas is supplied upward from the ejection hole 26, and the wafer W is loaded on the measuring stage 20 (step S6). As a result, the outer edge of the wafer W is supported by the tapered support surface 23 of the stage body 21, and the wafer W is loaded on the measuring stage 20 in such a way that the rear surface of the wafer W does not come in contact with the stage surface 22. The horizontal movement of the wafer W over the stage body 21 is restricted by the protrusions 24, thereby positioning the wafer W.

In the wafer surface measuring apparatus 100 according to this embodiment, the gas is supplied from the ejection hole 26 when the wafer W is loaded on the measuring stage 20 from the upward side. As a result, the center portion of the wafer W at the rear surface thereof is pressed upward by the pressure of the gas supplied from the ejection hole 26.

Therefore, the wafer W can be further bent in the upwardly convex shape by the weight of the wafer W and the pressure of the gas supplied from the ejection hole 26.

Here, for example, in the case in which the wafer carrying device 30 holds, for example, the outer peripheral portion of the wafer W, since the center portion of the wafer W is bent in downwardly convex shape, the center portion of the wafer W at the rear surface thereof may come in contact with the stage surface 22, before the outer edge of the wafer W is supported on the tapered support surface 23, at the loading time of the wafer W.

In this regard, in the wafer surface measuring apparatus 100 according to this embodiment, since the wafer W is bent in the upwardly convex portion, as described above, the outer edge of the wafer W firstly comes in contact with the tapered support surface 23 at the loading time of the wafer W. Consequently, it is possible to prevent the rear surface of the wafer W from coming in contact with the stage surface 22 at the loading time of the wafer W.

As described above, if the wafer W is loaded on the stage body 21, the supply of the pressurized gas to the Bernoulli chuck 40 of the wafer carrying device 30 is stopped, and thus the suction and holding of the wafer W by the Bernoulli chuck 40 is released.

Figure 8:
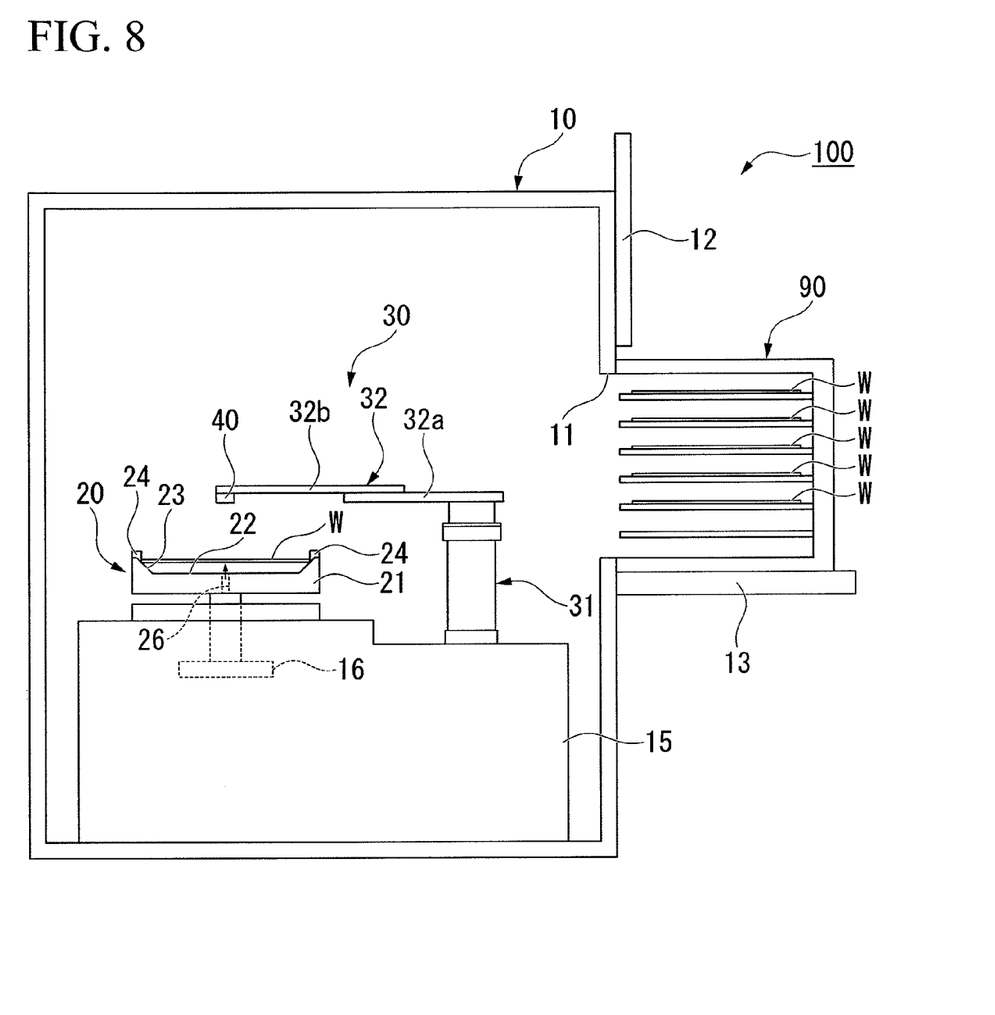
FIG. 8 is a diagram illustrating a state in which a wafer is loaded on a measuring stage.

In this instance, the wafer W is still bent in the upwardly convex position by the Bernoulli chuck 40, but due to the restoring force and its own weight, the center portion of the wafer W is deflected downward. If any countermeasures are not taken, the center portion of the wafer W is deflected downward, and thus comes in contact with the stage surface 22. In this regard, since the pressure of the gas supplied from the ejection hole 26 is controlled to be increased at the loading time of the wafer W, in comparison with the measuring time of the wafer W, the pressure can be strongly applied to the center portion of the wafer W upwardly at the rear surface thereof. As a result, when the suction and holding of the wafer W by the Bernoulli chuck 40 is released, it is possible to surely prevent the rear surface of the wafer W from coming in contact with the stage surface, as shown in FIG. 8, thereby supporting the wafer W horizontally.

After that, the wafer W is fixed by holding, for example, the edge of the surface of the wafer W with claw portions (not shown) on the stage body 21 (step S7).

In the state in which the supply of the gas from the ejection hole 26 is maintained, the stage body 21 is rotated by the rotary drive unit (step S8), and the wafer W loaded on the stage body 21 is irradiated with a laser beam on the surface of the wafer. And then, detection of particles and flaws is performed by detecting scattered light (step S9).

The measured wafer W is released from the fixation of the claw portions, and then the wafer sucked and held by the Bernoulli chuck 40 is transferred into the cassette 90. After that, a new wafer W is loaded and measured on the measuring stage 20 by the same process as the above process.

In this way, the wafer surface measuring apparatus 100 according to this embodiment surely can load the wafer on the measuring stage, while maintaining the non-contact state between the rear surface of the wafer W and the stage surface 22.

Although the wafer surface measuring apparatus 100 according to this embodiment is described, the invention is not limited thereto, and may be altered without departing from the scope of the technical thoughts of the invention.

Figure 9:
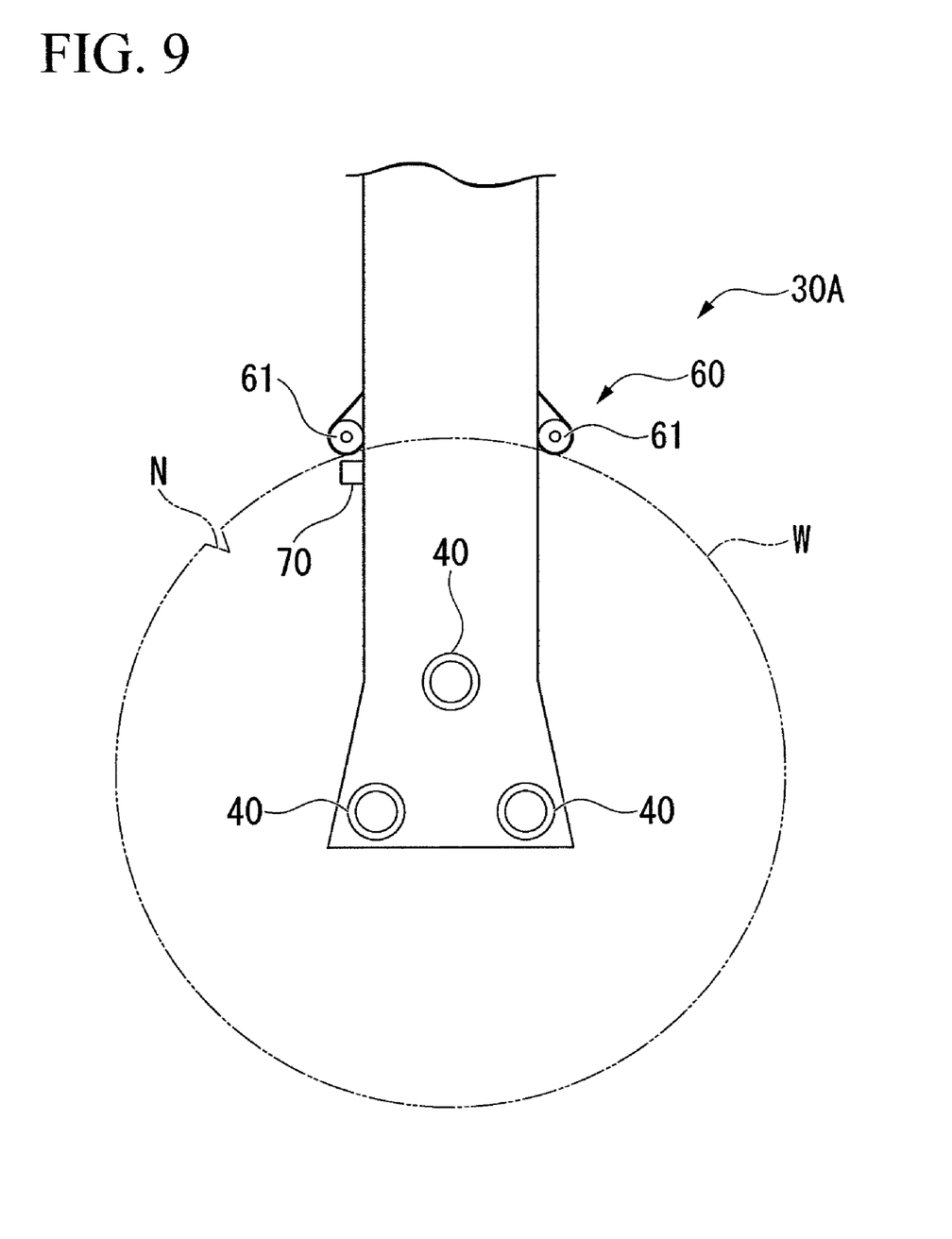
FIG. 9 is a plan view of a first modified example of a wafer carrying means.
Figure 10:
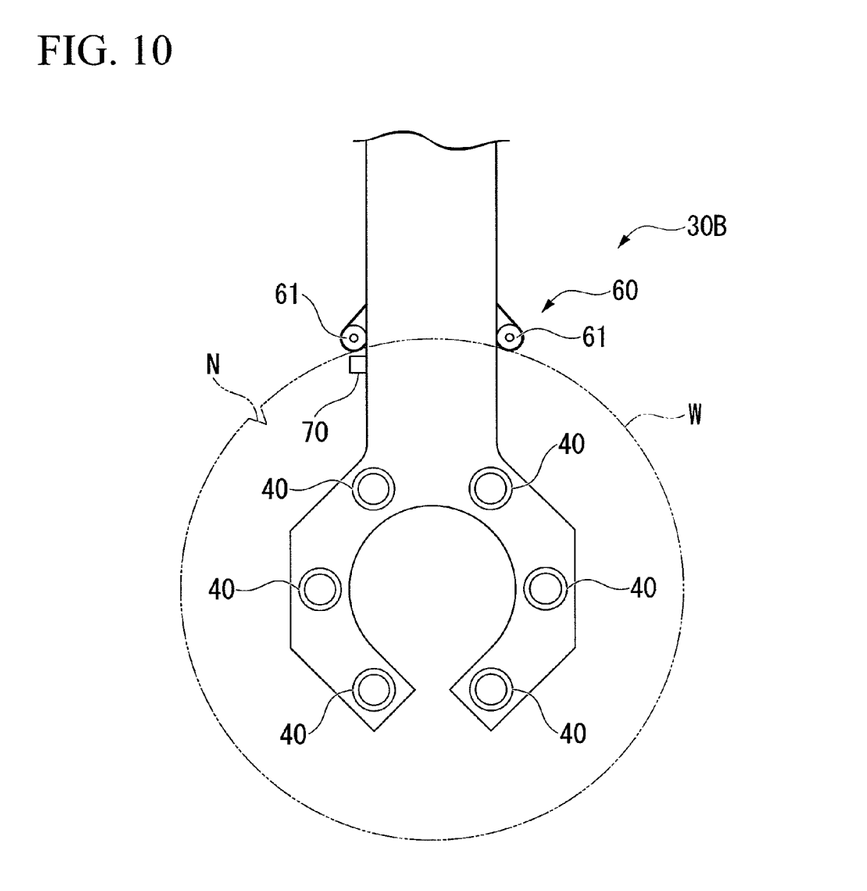
FIG. 10 is a plan view of a second modified example of a wafer carrying means.

For example, the wafer carrying device 30 may be constituted as shown in FIG. 9 or 10, as a modified example. As these modified examples, a plurality of Bernoulli chucks 40 are provided, and a rotational position adjusting means 60 and a notch sensor 70 are provided.

A wafer carrying device 30A shown in FIG. 9 includes three Bernoulli chucks 40 each disposed at a regular-triangular leg portion, and the centers of these three Bernoulli chucks 40 are positioned in the vicinity of the center portion of the wafer W so as to suck and hold the wafer W.

A wafer carrying device 30B shown in FIG. 10 includes six Bernoulli chucks 40 each disposed at a hexagonal leg portion, and the centers of Bernoulli chucks 40 are positioned in the vicinity of the center portion of the wafer W so as to suck and hold the wafer W.

The plurality of Bernoulli chucks 40 are set up, for example, in a half range of a radius of the wafer W, and thus the wafer W can be bent in an upwardly convex shape when the plurality of Bernoulli chucks 40 suck and hold the wafer W.

The wafer carrying devices 30A and 30B can suck and hold the wafer W easily and surely compared with the wafer carrying device including one Bernoulli chuck 40. The number of Bernoulli chucks 40 is not limited to 3 or 6, and other numbers of Bernoulli chucks may be employed. The plurality of Bernoulli chucks 40 are not limited to the regular-triangular or hexagonal leg portion, and may be displaced at other positions. Further, the Bernoulli chucks are not limited to the half range of the radius of the wafer W, and may be set up at positions which can support the wafer W.

In the wafer carrying devices 30A and 30B shown in FIGS. 9 and 10, the rotational position adjusting means 60 includes a pair of rollers 61 which come in contact with the outer edge of the wafer W when the wafer W is sucked and held by the Bernoulli chuck 40. For example, as the rollers 61 are rotated by a servo motor (not shown), the wafer W contacting the rollers 61 is rotated. Further, the notch sensor 70 is a sensor for detecting a notch N of the wafer W, and, for example, as shown in FIGS. 9 and 10, is provided at a position adjacent to the rollers 61.

According to the wafer carrying devices 30A and 30B having such a configuration, when the wafer W in the cassette 90 sucked and held by the Bernoulli chuck 40 is carried to the measuring stage 20, it is possible to easily perform the position alignment of the notch N by rotating the wafer W with the rotational position adjusting means 60 until the notch sensor 70 detects the notch N. Accordingly, since a notch aligning process needed separately up to now can be performed simultaneously with the carrying process of the wafer W, it is possible to promote work efficiency.

The rotational position adjusting means 60 and the notch sensor 70 may be installed to the wafer carrying device 30 having single Bernoulli chuck 40.

Figure 11:
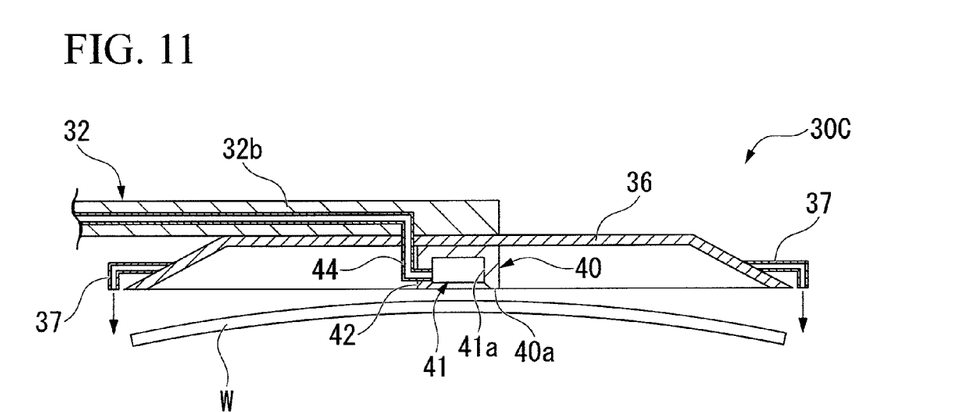
FIG. 11 is a cross-sectional view of a third modified example of a wafer carrying means.

In addition, for example, a wafer carrying device 30C having a configuration shown in FIG. 11 may be provided. The wafer carrying device 30C has a single Bernoulli chuck 40, similar to the wafer carrying device 30 of the above embodiment, and a cover 36 which covers the whole area of the surface of the wafer W when the wafer W is sucked and held. It is possible to prevent foreign substances from adhering on the surface of the wafer W by the cover 36, thereby maintaining the cleanliness of the surface of the wafer W. The cover 36 may be installed to the wafer carrying devices 30A and 30B having a plurality of Bernoulli chucks 40 shown in FIGS. 9 and 10. The shape of the cover 36 is not limited to a circular truncated cone, and other shapes may be employed.

In the case in which the cover 36 is installed, as shown in FIG. 11, a gas supplying means 37 may be installed so as to prevent invasion of ambient air between the cover 36 and the surface of the wafer W by supplying the gas when the wafer W is sucked and held. As a result, it is possible to prevent foreign substances from adhering on the surface of the wafer W more positively, thereby maintaining the cleanliness of the surface of the wafer W. The gas supplying means 37 may not be installed to the outside of the cover 36, but installed to the inside thereof.

Figure 12:
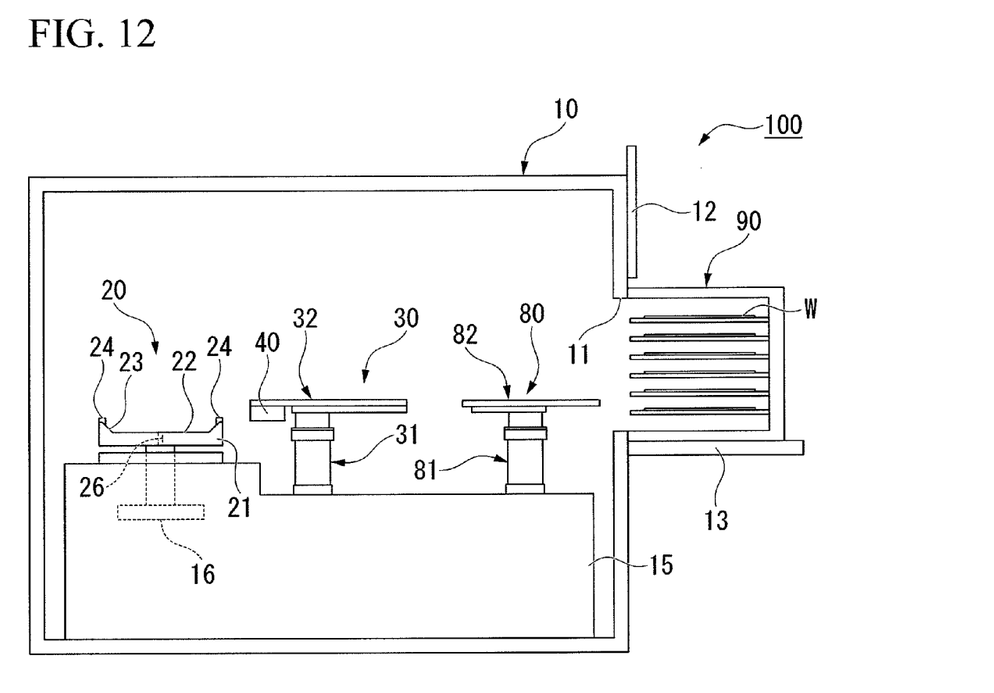
FIG. 12 is a configuration diagram schematically illustrating one example of a wafer surface measuring apparatus including a wafer discharging device.

According to the wafer surface measuring apparatus 100, in the case in which the wafer carrying device 30 has a size not so as to enter into the cassette 90, for example, a wafer discharging device (a wafer discharging means) 80 different from the wafer carrying device 30 may be installed, as shown in FIG. 12. The wafer discharging device 80 includes a movable post 81 and an arm 82, similar to the wafer carrying device 30. The arm 82 is formed to have a thickness so as to enter between the wafers W stacked in the cassette 90.

After the arm 82 of the wafer discharging device 80 enters in the cassette 90 and then takes out the wafer W, the Bernoulli chuck 40 of the wafer carrying device 30 sucks and holds the wafer W. In this way, in the case in which the arm 32 of the wafer carrying device 30 and the Bernoulli chuck 40 do not enter in the cassette 90, it is possible to carry the wafer W to the measuring stage 20.

In this embodiment, the Bernoulli chuck is selected as a chuck which sucks and holds the wafer W, but an electrostatic chuck can be selected as an other chuck which can suck and hold with maintaining the non-contact state between the surface of the wafer W and the chuck. In this case, "the non-contact state between the surface of the wafer W and the chuck" means the surface region of the wafer W which will be used as a device region does not contact with the chuck, when the chuck sucks and holds the wafer W, and means the chuck may be contact with such as a bevel of the wafer W which will not be used as a device region.

Figure 13:
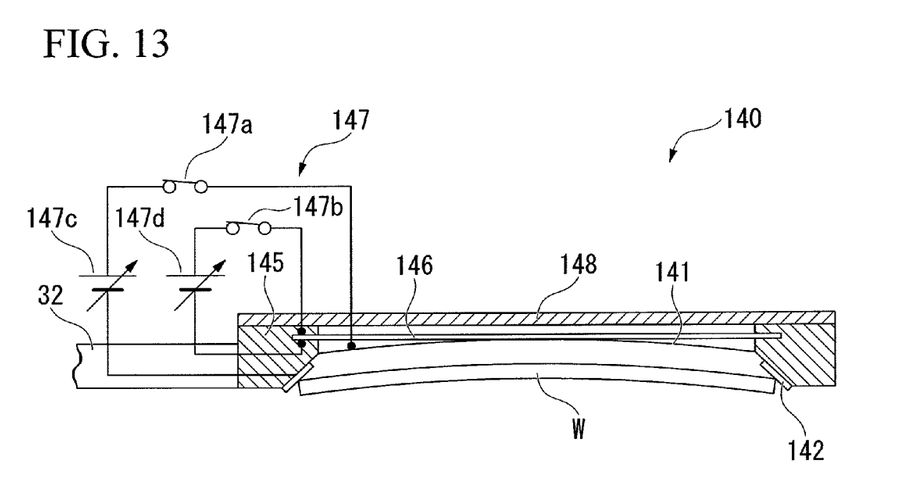
FIG. 13 is a cross-sectional view of an electrostatic chuck.

FIG. 13 is a cross-sectional view which shows an example that the wafer W in nearly-horizontal condition is sucked and held by an electrostatic chuck 140. In FIG. 13, the electrostatic chuck 140 includes an inner electrode 141 coated with a corrosive-resistant and metal-oxide-type insulating film over the surface, whose thickness is about 0.1 mm, and having a discoid shape, an outer electrode 142 which has same shape as the outer edge of the wafer W and is coated with wear resistant and low-dust-producing diamond thin layer over the surface, a correction actuator 146 consisting of a bimorph type piezo actuator which corrects the inner electrode 141, an electrode-maintaining ring 145 which keeps the inner electrode 141 and the outer electrode 142 being insulated, and an electrical means 147 for applying a voltage to the inner electrode 141 and the outer electrode 142, including an electrical source (not shown) and switch 147$a$, 147$b$, a variable resistance 147$c$, 147$d$, and a cover 148 which covers over the inner electrode 141. The outer electrode 142 may have a shape so as to contact with all around or a part of the outer edge of the wafer W if it produces an electrostatic condition enough to suck and hold the wafer W by the inner electrode 141 when a voltage is applied between the inner electrode 141 and the outer electrode 142.

The inner electrode 141 and the outer electrode 142 are held by the electrode-maintaining ring 145, so as to face the inner electrode 141 to the wafer W with inclusion space of from 0.2 to 0.3 mm, when the outer electrode 142 contacts with the outer edge of the wafer W. The electrostatic chuck 140 produces an electrostatic suction when a voltage of 500V is applied between the inner electrode 141 and the outer electrode 142. Therefore, the electrostatic chuck 140 sucks and holds the wafer W by an inner electrode 141 in contacting the outer edge of the wafer W and an outer electrode 142. In this case, by putting an electrode correction actuator 146 in action, the inner electrode 141 is corrected and deformed as a same form that the wafer W is bent owing to suction. By the method, it is possible to suck and hold the wafer W in a non-contact manner and bend the wafer W in an upwardly convex shape.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A wafer surface measuring apparatus which measures a surface of the wafer by irradiating a laser beam on a wafer comprising:
    a measuring stage that supports an outer edge of the wafer and loads the wafer in a manner not contacting with a rear surface of the wafer and a stage surface;
    a wafer carrying means that moves the wafer over the measuring stage and loads the wafer on the measuring stage from an upward side;
    a rotary drive unit which rotates the measuring stage; and
    an ejection hole formed at a center portion of the stage surface to supply gas to a rear surface of the wafer loaded on the measuring stage,
    wherein the wafer carrying means includes a chuck which sucks and holds the surface of the wafer in a non-contact manner and bends the wafer in an upwardly convex shape.

2. The wafer surface measuring apparatus according to claim 1, wherein when the wafer is loaded on the measuring stage by the wafer carrying means, the gas is supplied from the ejection hole.

3. The wafer surface measuring apparatus according to claim 2, wherein when the wafer is loaded on the measuring stage, pressure of the gas supplied from the ejection hole is set to be higher than pressure of the gas supplied from the ejection hole at measuring time of the wafer.

4. The wafer surface measuring apparatus according to claim 1, wherein the wafer carrying means includes a rotational position adjusting means for displacing a rotational position of the wafer, and a notch sensor for detecting a position of a notch of the wafer.

5. The wafer surface measuring apparatus according to claim 1, wherein the chuck is an electrostatic chuck.

6. The wafer surface measuring apparatus according to claim 1, wherein the chuck is a Bernoulli chuck.

7. The wafer surface measuring apparatus according to claim 6, wherein the pressurized gas supplied to the Bernoulli chuck is clean gas having cleanliness after the pressurized gas passes through an air filter.

8. The wafer surface measuring apparatus according to claim 1, wherein the wafer carrying means includes a cover having a diameter larger than the wafer so as to cover the whole area of the wafer when seen from a plan view, and being installed in parallel with the wafer in a facing state when the main surface of the wafer is horizontally held at an upper side.

9. The wafer surface measuring apparatus according to claim 8, wherein the wafer carrying means includes a gas supplying means for supplying gas to prevent ambient air from entering between the cover and the surface of the wafer.

10. The wafer surface measuring apparatus according to claim 1, further comprising a wafer discharging means for discharging the wafer from a cassette with the plurality of wafers received therein,
    in which the wafer carrying means sucks and carries the wafer discharged from the cassette by the wafer discharging means.

* * * * *